United States Patent [19]

Adams

[11] Patent Number: 5,336,841
[45] Date of Patent: Aug. 9, 1994

[54] OXYGENATE REMOVAL IN MTBE PROCESS

[75] Inventor: John R. Adams, Pasadena, Tex.

[73] Assignee: Chemical Research & Licensing Company, Pasadena, Tex.

[21] Appl. No.: 42,716

[22] Filed: Apr. 5, 1993

[51] Int. Cl.$^5$ .............................................. C07C 7/10
[52] U.S. Cl. .................................... 585/834; 585/833; 203/28; 203/DIG. 6
[58] Field of Search ................... 585/834, 833; 203/28, 203/DIG. 6

[56] References Cited

U.S. PATENT DOCUMENTS

| | | | |
|---|---|---|---|
| 4,232,177 | 11/1980 | Smith, Jr. ............................ | 585/639 |
| 4,307,254 | 12/1981 | Smith ................................. | 568/697 |
| 4,336,407 | 6/1982 | Smith ................................. | 568/697 |
| 4,447,668 | 5/1984 | Smith, Jr. et al. ................... | 585/639 |
| 4,482,775 | 11/1984 | Smith ................................. | 585/671 |
| 4,504,687 | 3/1985 | Jones ................................. | 568/697 |
| 4,918,243 | 4/1990 | Smith ................................. | 568/697 |
| 5,122,236 | 6/1992 | Smith, Jr. et al. ................... | 585/833 |

*Primary Examiner*—Anthony Mc Farlane
*Assistant Examiner*—Nhat D. Phan
*Attorney, Agent, or Firm*—Kenneth H. Johnson

[57] ABSTRACT

A process is provided to remove oxygenates from a C$_4$ raffinate stream from an MTBE plant. A back-cracking catalyst is placed into the bottom of an oxygenate removal column which will convert any MTBE or TBA contained therein back to their original components of isobutene and methanol or water. The raffinate stream is first subjected to a water wash to remove the gross amounts of methanol and DME.

5 Claims, 1 Drawing Sheet

OXYGENATE REMOVAL IN MTBE PROCESS

BACKGROUND OF THE INVENTION

1. Field of the Invention

The present invention relates generally to a process for the recovery of n-butenes from methyl tertiary butyl ether (MTBE) made by the reaction of methanol with isobutene contained within a mixed $C_4$ stream containing isobutene, normal butene and butanes. More particularly the invention relates to a catalytic distillation process which includes an oxygenate removal unit wherein light ends and light oxygenated compounds are separated from unreacted $C_4$'s utilizing a distillation column. Most particularly, the invention relates to the use of a catalyst in the lower end of the oxygenate recovery column to convert heavier oxygenated compounds, such as MTBE and tertiary butyl alcohol (TBA) back to their constituent components for ease of separation.

2. Related Art

The production of ethers by the reaction of an isoolefin and an alcohol is a well known, e.g., U.S. Pat. Nos. 3,121,124; 3,270,081; 3,170,000; 3,629,478 and 3,634,534. One commercial operation utilizes the simultaneous reaction and distillation of the products from the reactants. This procedure has become known as catalytic distillation and has been adapted to MTBE production as disclosed in U.S. Pat. Nos. 4,232,177; 4,307,254; 4,336,407; 4,504,687 and 4,918,243. In the catalytic distillation process the catalyst is part of the distillation system acting as both catalyst and distillation structure. In addition to the above cited patents specific catalytic distillation structures are disclosed in commonly assigned U.S. Pat. Nos. 4,215,011; 4,242,530; 4,302,356; 4,443,559 and 4,482,775.

Briefly, a preferred and commercial catalyst structure described in the catalytic distillation process comprises a cloth belt with a plurality of pockets spaced along the belt and containing particulate catalyst material, said cloth belt being wound in a helix about a spacing material such as stainless steel knitted mesh. These units are then disposed in the distillation column reactor. In addition, commonly assigned U.S. Pat. Nos. 4,443,559 and 4,250,052 disclose a variety of catalyst structures for this use and are incorporated herein.

Since the feed in MTBE production is generally a mix $C_4$ stream, there is usually a $C_4$ stream, e.g. n-butenes separated and purified for other use.

The separation of the reactants from the ether products is fairly efficient. However, the unreacted methanol and $C_4$'s which are taken overhead must then be separated. This presents somewhat of a problem because methanol forms various azeotropes in the $C_4$ stream depending upon the pressure. Dimethyl ether (DME) is also a usual by-product.

In acid alkylations one problem caused by the presence of dimethyl ether (DME) and other oxygenated compounds is the use of more acid than the alkylation per se. In the case of sulfuric acid alkylations this may be a tolerable detriment, however, in the case of HF alkylations an acid soluble oil is formed which interferes with the separation of the alkylate product from the acid and may lead to fouling of the alkylation unit.

One common way to separate the methanol from the $C_4$ stream utilizes distillation and water washing the mixture of $C_4$ and methanol to remove the methanol. The water washing step leaves residual amounts of methanol (up to 2 wt %.), MTBE (50 ppm) and DME (500 ppm). The water wash could remove the DME but would require excessive amounts of wash water. This final water washed product is distilled to remove the DME and methanol.

One method of removing all oxygenated compounds is to subject the mixture to an adsorbent bed of molecular sieve or silica gel. See for example U.S. Pat. No. 4,814,517. Additionally, U.S. Pat. Nos. 4,575,566 and 4,575,567 disclose the use and regeneration of such adsorbents.

Another method is disclosed in and commonly assigned U.S. Pat. No. 5,122,236. The process disclosed therein utilizes the distillation column prior to the water wash step, but takes up to 40% overheads which insures that essentially all of the methanol and DME are taken overhead. The overheads are then condensed and subjected to the water wash which requires less water because of the smaller volume. The hydrocarbons in the condensed overheads are separated from the water phase containing the DME and methanol and returned to the distillation column.

However, to utilize either of the distillation techniques it is necessary to insure that there are no heavy oxygenates, such as MTBE or TBA (another by product of the MTBE process) present in the feed to the column as they would simply be taken out with the bottoms in the $C_4$ product stream.

SUMMARY OF THE INVENTION

Briefly, the invention covers a process which utilizes a water wash to separate the methanol from the $C_4$ raffinate after exposure to the catalyst. While the separation of the reactants (methanol and $C_4$'s) from the product MTBE is fairly efficient by distillation, there may still be minor amounts in the overheads along with some dimethyl ethers and/or TBA. In order to dispense with special heavy oxygenate removal sections, such as a mole sieve, the present invention provides a catalytic distillation section in the lower end of the oxygenate removal distillation column. A catalyst is used which will decompose the MTBE and TBA back to their constituent components which are methanol, isobutene and water. The methanol can then be recycled back to the etherification reactor and the isobutene recovered with the other $C_4$'s.

BRIEF DESCRIPTION OF THE DRAWING

The FIGURE is a flow diagram in schematic of one embodiment of the present invention.

DESCRIPTION OF THE PREFERRED EMBODIMENTS

Figure 1:
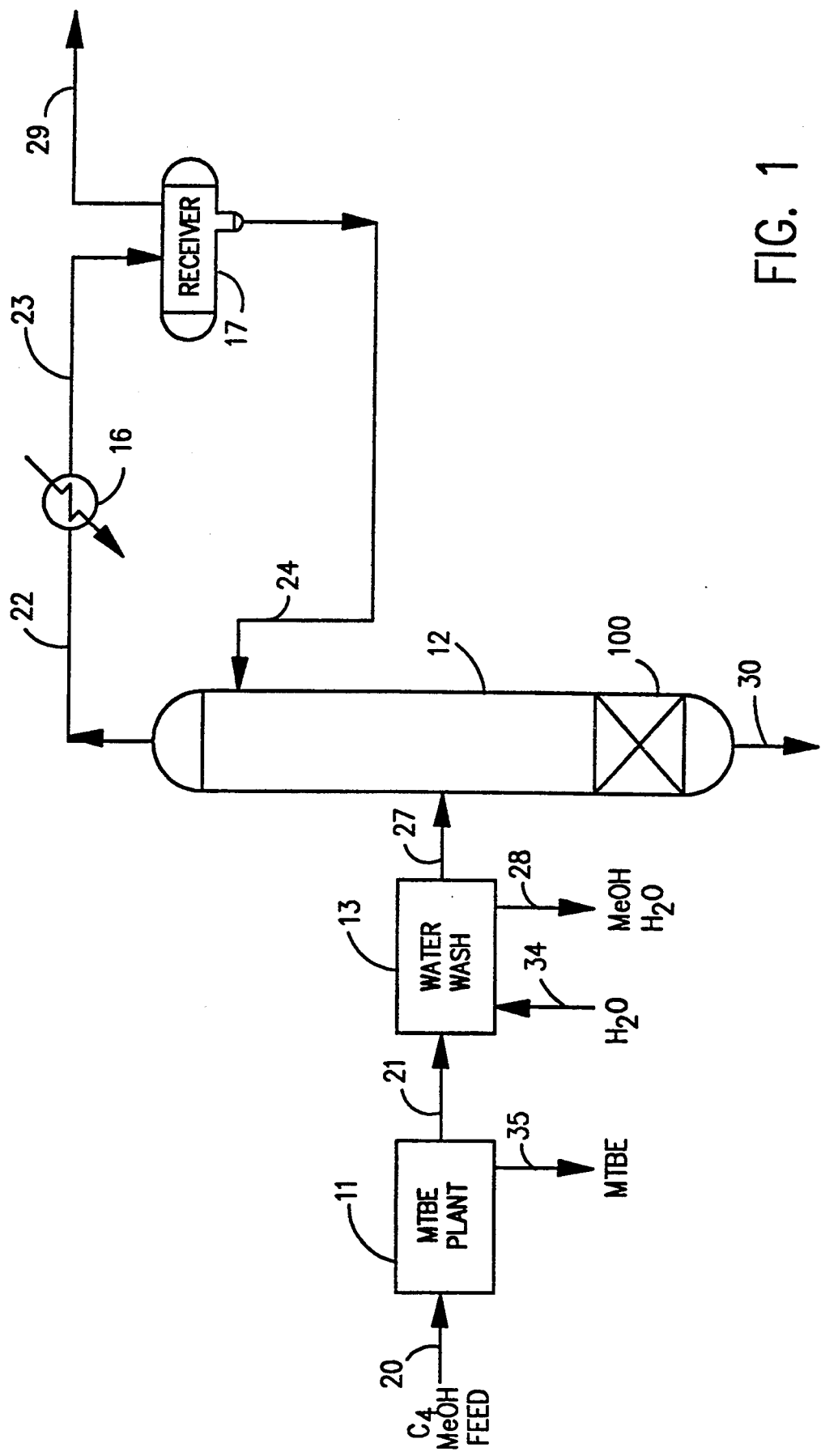

The present invention may be used with any of the reactors or methods of producing MTBE known in the art, comprising reacting methanol with isobutene in a mixed $C_4$ stream.

The methanol may be present in stoichiometric amounts or in excess or deficiency thereof based on the isobutene in the $C_4$ feed. The reaction of the isobutene and methanol is selective, that is, the n-butenes are far less reactive than the isobutene. The acid catalyst now widely used are the acidic cation exchange resins.

The hydrocarbon feed to the oxygenate removal distillation column is the residual stream from an MTBE process, or any other process which will leave DME, methanol, MTBE or TBA as impurities usually in amounts of 5 weight percent or less. Such streams used for producing MTBE are mixed C$_4$ streams containing principally isobutane (I-C$_4$), normal butane (n-C$_4$) butene (B-1), isobutene (I-B), trans butene-2 (TB-2) and cis butene-2 (CB-2) (plus some minor impurities including butadiene, C$_3$'s and C$_5$'s). The C$_4$ hydrocarbon feed stream in the present process is substantially the same stream with a reduced amount of isobutene from MTBE manufacture and the DME, MTBE, TBA and methanol impurities. There are several processes for producing MTBE and the feed streams vary in the specific ratios of C$_4$, e.g. isobutene may vary from about 5 to 100 wt. %, generally up to 60 wt. % of the MTBE feed. Also the degree of isobutene conversion varies in the processes, but are generally operated commercially to obtain 85%+ conversion. The DME, methanol, TBA and MTBE may comprise up to 5 wt. % of the stream once the MTBE is removed, but usually they would constitute less than 1 wt % of the residual C$_4$ stream.

In the embodiment illustrated in the FIGURE the residual stream 21 from the MTBE plant 11 is first subjected to a water wash 13 to remove the majority of the methanol and minor amounts of the DME prior to introduction into the distillation column reactor 12 used for the oxygenate removal column. Stream compositions are shown in TABLE I. The feed 27 in this case contains about 500 wppm DME, 400 wppm water, 10 wppm methanol, 510 wppm MTBE and perhaps up to 10 wppm TBA.

The location of the feed into the oxygenate removal distillation column 12 of the present invention is not critical, but is preferable to have the feed into the middle portion of the column. The bed 100 of catalytic distillation structure is preferably located in the lower end of the column.

The catalyst used is any one of several of the "back-cracking" types currently available that will convert MTBE and TBA back into their original components, i.e. methanol, isobutene and water. One such dissociation catalyst is an metal modified acid ion exchange resin and is described in U.S. Pat. No. 4,629,710, or the acid ion exchange resin as disclosed in U.S. Pat. No. 3,121,124.

Briefly the metal modified catalyst compositions described therein are nuclear sulfonic acid solid resins which have at least 50% of the sulfonic acid groups neutralized with metal ions of Group 4b, 5b, 7b, 8 or 2b, and of the Periodic Table of elements, the rare earth metals or mixtures thereof, and the balance of the sulfonic acid groups neutralized with an alkali metal or alkaline earth metal, ammonium or mixtures thereof. The preferred metals are Ti, V, Cr, Mn, Fe, Co, Ni, Cu, Zn, Zr, Nb, Mo, Ru, Rh, Pb, Ag, Cd, Ta, W, Re, Pl, Ce, Nd, Sm, and Eu. Other dissociation catalysts are aluminum compounds supported on silica (U.S. Pat. No. 4,398,051), phosphoric acid on various supports (U.S. Pat. No. 4,320,232), metal containing weak acids (UK patent 1,173,128), carriers (U.S. Pat. No. 4,398,051), H$_2$SO$_4$ treated clay U.S. Pat. No. 4,254,290 and HF treated clay (U.S. Pat. No. 4,691,073).

The catalysts may be most conveniently utilized as part of a catalytic distillation structure such as described herein above, i.e. contained within pockets on a cloth belt and intertwined with a support material such as stainless steel mesh and placed into the column to form the distillation reaction zone 100.

The distillation column reactor 12 is preferably operated at 200 to 300 psig and the temperature in the overhead is that of the lowest boiling component at the pressure employed with a temperature in the bottom section being that of the highest boiling components. The decomposition of the trace amounts of MTBE and TBA is catalyzed in the distillation reaction zone by the dissociation catalyst to form methanol, isobutene and water. The methanol thus formed will be removed with the overheads 22 along with the DME and C$_3$'s with the isobutene being formed immediately being distilled away from the catalyst as liquid with the C$_4$ bottoms 30.

Because of the closeness of the boiling points of the C$_4$'s in the feed to the column the overhead 22 composition will comprise all the C$_4$ components, albeit in somewhat different ratios than the feed. The DME and methanol being the lowest boiling components (also any C$_3$'s) are substantially all in the overhead 22. The DME and/or methanol in the bottoms 30 is less than 10 parts per million. Substantially all of the MTBE or TBA is converted leaving essentially none in either the overheads 22 or bottoms 30.

The C$_4$ hydrocarbon feed stream 27 is fed near the middle of distillation column 12, which for the purpose of this illustration is a 25 tray reaction distillation column with a bed of the back-cracking catalyst 100 in the form of a catalytic distillation structure in the lower section of the column, operated at 250 psig. The C$_4$ hydrocarbon overhead fraction 22 has a temperature of about 100° C. The vaporous stream 22 passes through condenser 16 (also operated at 250 psig) where it is condensed and cooled to about 40° C. and collected via 23 in receiver 17 (at 250 psig). Substantially the entire overhead is condensed. The condensed overhead, i.e., hydrocarbon fraction now having a reduced DME and methanol content compared to that in line 27 passes through line 24 back to distillation tower 12 as reflux. Light ends (lower boiling then C$_4$'s are removed via line 29.

The bottoms 30 from distillation column 12 are substantially free of DME and methanol and may be recovered for further use.

Such elements as reboilers, valves, compressors, etc. have been omitted, but the appropriate insertion in normal engineering practice would be obvious expedients.

TABLE I

| Component Lbs/hr | STREAM | | | | |
|---|---|---|---|---|---|
| | 20 | 21 | 22 | 27 | 30 |
| Isobutene | 21421 | 536 | 250 | 536 | 286 |
| Other C$_4$ (includes C$_3$ and C$_5$) | 97987 | 97935 | 7800 | 97900 | 90100 |
| Methanol | 13710 | 1616 | 1 | 1 | 0 |
| DME | — | 18 | 15 | 15 | 0 |
| MTBE | — | 1 | 0 | 1 | 0 |
| TBA | — | 0.5 | 0 | 1 | 0 |
| Water | — | — | 39 | 39 | 0 |

The invention claimed is:

1. A process for removing dimethyl ether (DME), methyl tertiary butyl ether (MTBE), tertiary butyl alcohol (TBA), methanol or mixtures thereof from a C$_4$ hydrocarbon stream comprising:

(a) feeding a substantially normal C$_4$ hydrocarbon feed stream containing minor amounts of dimethyl ether (DME), methyl tertiary butyl ether (MTBE), tertiary butyl alcohol (TBA), methanol or mixtures thereof to a distillation column reactor; and (b) simultaneously in said distillation column reactor:
(i) contacting said methyl tertiary butyl ether (MTBE) and tertiary butyl alcohol (TBA) with a dissociation catalyst in the form of a catalytic distillation structure thereby decomposing at least a portion of the methyl tertiary butyl ether (MTBE) and tertiary butyl alcohol (TBA) to form a decomposition product comprising isobutene, methanol and water, and
(ii) fractionating the feed stream and decomposition product in said distillation column reactor to provide a vaporous overhead fraction containing hydrocarbons and substantially all of the dimethyl ether (DME) and methanol and a liquid bottoms fraction containing substantially less dimethyl ether (DME), methyl tertiary butyl ether (MTBE), tertiary butyl alcohol (TBA) and methanol than said feed stream.

2. The process according to claim 1 wherein said vaporous overhead fraction comprises from about 20 to 40 volume percent of said feed stream and further comprising the steps of,
(c) condensing the vaporous overhead fraction to form a liquid overhead fraction, and
(d) returning a portion of the liquid overhead fraction to said distillation column.

3. The process according to claim 2 wherein steps (a) through (d) are operated at a pressure in the range of 200 to 300 psig.

4. The process according to claim 3 wherein said liquid overhead fraction is cooled to a temperature in the range of 20° C. to 50° C.

5. The process according to claim 2 wherein said liquid overhead fraction of step (d) comprises substantially all of the hydrocarbons contained in the vaporous overhead fraction of step (b) (ii).

* * * * *